US012805828B2

(12) United States Patent
Seppä

(10) Patent No.: US 12,805,828 B2
(45) Date of Patent: Nov. 24, 2026

(54) AUDIO HEAD, SENSOR HEAD, DEVICE AND METHOD OF ANALYZING PROPERTY OF TARGET USING SAME

(71) Applicant: Sonai Health Oy, Espoo (FI)

(72) Inventor: Heikki Seppä, Espoo (FI)

(73) Assignee: Sonai Health Oy, Espoo (FI)

( * ) Notice: Subject to any disclaimer, the term of this patent is extended or adjusted under 35 U.S.C. 154(b) by 162 days.

(21) Appl. No.: 18/844,263

(22) PCT Filed: Mar. 28, 2023

(86) PCT No.: PCT/FI2023/050172
§ 371 (c)(1),
(2) Date: Sep. 5, 2024

(87) PCT Pub. No.: WO2023/198955
PCT Pub. Date: Oct. 19, 2023

(65) Prior Publication Data

US 2025/0176930 A1 Jun. 5, 2025

(30) Foreign Application Priority Data

Apr. 11, 2022 (FI) ..................................... 20225315

(51) Int. Cl.
*A61B 7/04* (2006.01)
*H04R 1/46* (2006.01)
*H04R 3/04* (2006.01)

(52) U.S. Cl.
CPC ................. *A61B 7/04* (2013.01); *H04R 1/46* (2013.01); *H04R 3/04* (2013.01)

(58) Field of Classification Search
CPC ......... A61B 7/04; A61B 8/0883; A61B 8/444; A61B 8/4477; A61B 8/54; A61B 8/4281; A61B 8/4444; H04R 1/46
(Continued)

(56) References Cited

U.S. PATENT DOCUMENTS 5,817,020 A 10/1998 Ishii et al.
2013/0336095 A1 12/2013 Seppa et al.
(Continued)

OTHER PUBLICATIONS

European Patent Office, International Search Report, International Application No. PCT/FI2023/050172, mailed Jun. 21, 2023, 2 pages.
(Continued)

*Primary Examiner* — George C Monikang
(74) *Attorney, Agent, or Firm* — Ziegler IP Law Group, LLC.

(57) ABSTRACT

Disclosed is an audio head. The audio head includes a body having first cavity, first cavity having an open end and closed end opposite to open end separated by length L1, audio unit arranged on closed end, wherein audio unit is configured to provide first audio signal, first audio signal having a first frequency, and receive second audio signal, and controller configured to adjust first frequency to resonance frequency value determined by dimensions of first cavity, and determine acoustic impedance of target, arranged to be in contact with open end when in use, using first audio signal and second audio signal, wherein second audio signal comprises at least a part of first audio signal that is reflected back from target.

14 Claims, 6 Drawing Sheets

(58) Field of Classification Search
USPC .............................................................. 381/67
See application file for complete search history.

(56) References Cited

U.S. PATENT DOCUMENTS

| | | | | |
|---|---|---|---|---|
| 2016/0074017 | A1* | 3/2016 | Lee .......................... | A61B 8/14 600/443 |
| 2019/0277805 | A1 | 9/2019 | Wrobel | |
| 2020/0329977 | A1 | 10/2020 | Freeman et al. | |
| 2021/0278530 | A1 | 9/2021 | Haque et al. | |

OTHER PUBLICATIONS

European Patent Office, Notification of Transmittal of The International Search Report and the Written Opinion of the International Searching Authority, or the Declaration, International Application No. PCT/FI2023/050172, mailed Jun. 21, 2023, 11 pages.
Finnish Patent and Registration Office, Office Action, Patent application No. 20225315, dated Nov. 28, 2022, 9 pages.
Xu, T. et al. Equivalent Circuit Models of Cell and Array for Resonant Cavity-Based Piezoelectric Micromachined Ultrasonic Transducer. In: IEEE Transactions on Ultrasonics, Ferroelectrics, and FrequencyControl May 11, 2020, vol. 67, No. 10, 2103-2118.

* cited by examiner

AUDIO HEAD, SENSOR HEAD, DEVICE AND METHOD OF ANALYZING PROPERTY OF TARGET USING SAME

TECHNICAL FIELD

The present disclosure relates to medical devices; and more specifically, to an audio head, a sensor head comprising one or more audio heads, and a method of analysing a property of a target. The present disclosure also relates to a device for measuring a property of a heart, such as various heart related information.

BACKGROUND

In the recent past, several diseases (such as heart disease) have been steadily rising across the globe. Therefore, a proper diagnosis of these diseases is required for an effective treatment, control, and measurement of parameters related to the disease in the subject's body. In this regard, several medical devices are being used to carry out an efficient diagnosis of various diseases in the subject's body.

Generally, the medical devices such as an invasive device may be used for the diagnosis of the diseases. In this regard, the invasive devices may employ a probe or a needle to be inserted inside a subject's body for measuring various parameters associated with the disease. However, the invasive devices may be a painful experience to the patient both during and post the measurement process. Alternatively, a non-invasive medical device may be used to diagnose the diseases. Such non-invasive device may include for example an X-ray, a sensor-based device (such as an electrocardiogram), an ultrasonic device, and so forth. Notably, existing non-invasive devices may employ different mediums, such as harmful radiations, electrical stimulation, and gels, during diagnosis, for example in X-ray, electrocardiogram and ultrasonography devices. It will be appreciated that amongst the above-mentioned mediums, frequent exposure to harmful radiations such as X-rays may lead to various side effects in the subject's body. Moreover, conventional non-invasive ultrasonic devices may require a medium such as a gel to get measurement done thereby. However, the use of gels may lead to an unpleasant experience by the subject. Moreover, the existing non-invasive devices, including the ultrasonic devices, may also fail to diagnose or reflect performance of an organ (such as a heart) in the subject's body in an effective manner. Furthermore, some examinations of the disease using the said devices may require special preparation beforehand as well as specially-trained technicians or medical professionals for performing the measurement.

Therefore, in light of the foregoing discussion, there exists a need to overcome the aforementioned drawbacks of conventional medical devices for diagnosis of various diseases, such as heart diseases.

SUMMARY

The present disclosure seeks to provide an audio head. The present disclosure also seeks to provide a sensor head. The present disclosure also seeks to provide a method of analysing a property of a target. The present disclosure also seeks to provide a device for measuring a property of a heart. An aim of the present disclosure is to provide a solution that overcomes at least partially the problems encountered in prior art, and provides an improved medical device for measuring the property of the target, such as the heart, in a non-invasive manner.

In one aspect, an embodiment of the present disclosure provides an audio head comprising

- a body having a first cavity, the first cavity having an open end and a closed end opposite to the open end separated by a length L1;
- an audio unit arranged on the closed end, wherein the audio unit is configured to
  - provide a first audio signal, the first audio signal having a first frequency, and
  - receive a second audio signal; and
- a controller configured to
  - adjust the first frequency to a resonance frequency value determined by the dimensions of the first cavity; and
  - determine acoustic impedance of a target, arranged to be in contact with the open end when in use, using the first audio signal and the second audio signal, wherein the second audio signal comprises at least a part of the first audio signal that is reflected back from the target.

In another aspect, an embodiment of the present disclosure provides a sensor head comprising one or more audio heads.

In yet another aspect, an embodiment of the present disclosure provides a method of analysing a property of a target, the method comprises

- arranging an open end of an audio head in contact with the target;
- providing a first audio signal from an audio unit of the audio head towards the target, the first audio signal having a first frequency;
- receiving a second audio signal from the target towards the audio unit; and
- operating a controller configured to
  - adjust the first frequency to a resonance frequency value determined by the dimensions of a first cavity of the audio head, and
  - determine acoustic impedance of the target, arranged to be in contact with the open end when in use, using the first audio signal and the second audio signal, wherein the second audio signal comprises at least a part of the first audio signal that is reflected back from the target.

In still another aspect, an embodiment of the present disclosure provides a device for measuring a property of a heart, the device comprising an audio head of aforementioned claims.

Embodiments of the present disclosure substantially eliminate or at least partially address the aforementioned problems in the prior art, and enable an improved method of analysing a property of a target. It will be appreciated that an audio head and a sensor head are used to determine acoustic impedance of the target, such as the skin and underlying organs, such as heart, thereunder. Beneficially, the determined acoustic impedance aids in analysing a property of the target and measuring parameters that may be associated with a potential disease or condition of the target.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1:
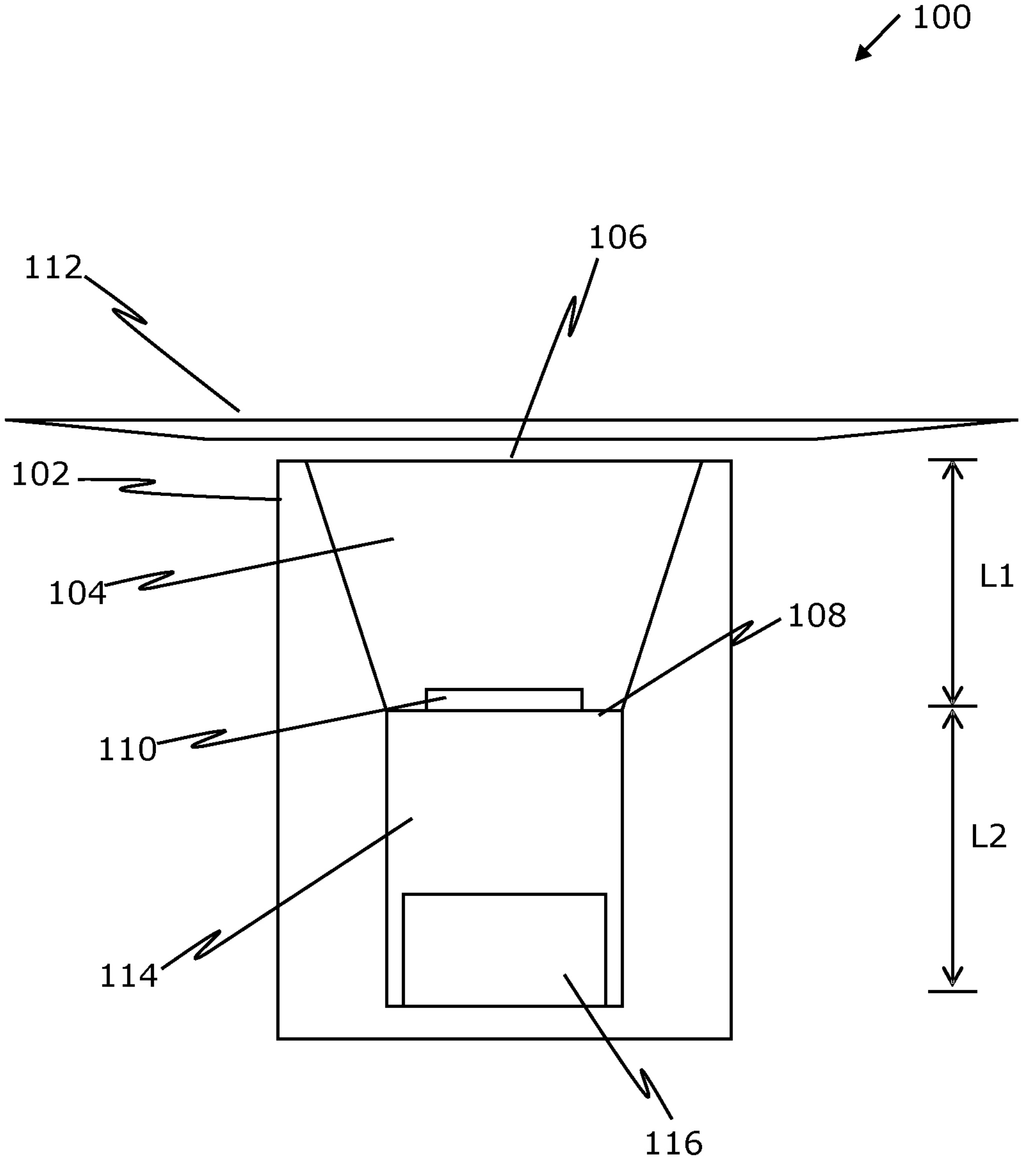
FIG. 1 is a schematic illustration of an audio head, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides an audio head comprising

- a body having a first cavity, the first cavity having an open end and a closed end opposite to the open end separated by a length L1;
- an audio unit arranged on the closed end, wherein the audio unit is configured to
  - provide a first audio signal, the first audio signal having a first frequency, and
  - receive a second audio signal; and a controller configured to
  - adjust the first frequency to a resonance frequency value determined by the dimensions of the first cavity; and
  - determine acoustic impedance of a target, arranged to be in contact with the open end when in use, using the first audio signal and the second audio signal, wherein the second audio signal comprises at least a part of the first audio signal that is reflected back from the target.

In another aspect, an embodiment of the present disclosure provides a sensor head comprising one or more audio heads.

In yet another aspect, an embodiment of the present disclosure provides a method of analysing a property of a target, the method comprises

- arranging an open end of an audio head in contact with the target;
- providing a first audio signal from an audio unit of the audio head towards the target, the first audio signal having a first frequency;
- receiving a second audio signal from the target towards the audio unit; and
- operating a controller configured to
  - adjust the first frequency to a resonance frequency value determined by the dimensions of a first cavity of the audio head, and
  - determine acoustic impedance of the target, arranged to be in contact with the open end when in use, using the first audio signal and the second audio signal, wherein the second audio signal comprises at least a part of the first audio signal that is reflected back from the target.

In still another aspect, an embodiment of the present disclosure provides a device for measuring a property of a heart, the device comprising an audio head of aforementioned claims.

The present disclosure provides the aforementioned audio head, the aforementioned sensor head, the aforementioned method of analysing the property of the target, and the aforementioned device for measuring the property of the heart. The body of the audio head forms a resonator volume when in use against the target for measuring acoustic signals from the target, i.e. the skin or any underlying organ. Beneficially, the determined acoustic signals aids in analysing a property of the target and measuring parameters that may be associated with a potential disease or condition of the target. Additionally, one or more audio heads (associated with the sensor head) enables measuring parameters from different angles and may even be used to generate a multi-dimensional simulation model of the target by combining the measured parameters from different angles. Moreover, an application of the aforementioned audio head may be extended to the devices for measuring the property of the heart in particular. Furthermore, the aforementioned method is an efficient way of analysing one or more properties of the target by significantly reducing or completely eliminating signal to noise ratio during measurements.

The term "audio head" as used herein refers to an acoustic medical device for listening to sounds of a target generally inside a subject's body as well as providing audio signal (such as ultrasonic signal) towards the subject's body. Herein, the subject may be a human, an animal or a corpse thereof. In other words, the audio head may be an electronic device, an acoustic device, or a combination thereof, that converts acoustic audio waves to electrical signals that may then be amplified and processed for analysis of the target. The audio head can be also used to generate audio signal. The audio head, in present disclosure, is indeed a surface/element, which can create movement to move air to produce audio signal and the same surface can be used to receive ("listen) audio.

The term "target" as used herein refers to an object whose properties could be measured using the audio head. Optionally, the target may be an organ of the subject that is under diagnosis. Optionally, the target may be a skin of the subject under which lies an organ of interest, such as a heart, lungs, a reproductive organ, a digestive organ, and the like. Optionally, the target may be a human heart. Optionally, the target may be an entire space that the audio head may sense. Optionally, the target may be a close object, such as ribs of subject's body that may be visible in an imaginary component of any other desired target, such as heart.

The audio head comprises the body having the first cavity, the first cavity having the open end and the closed end opposite to the open end separated by a length L1. The term "body" as used herein refers to a part of the audio head enclosing one or more other components. The term "first cavity" as used herein refers to an unfilled or a hollow space within the body of the audio head. Herein, the body has a wall defined over a certain length, such as the length L1, between two or more opposite ends, such as the open end and the closed end, enclosing the hollow space, namely, the first cavity, therebetween. Optionally, the cross-section of the body may be selected from any of: an elongated round shape, a polygonal shape (such as hexagonal, triangular prism shapes, cuboidal shape, and so on) or any other suitable shape. Moreover, based on the cross-section of the body, the body may comprise one or more side walls arranged between the open end and the closed end. In an example, for a cuboidal cross-section, the body has 4 side walls arranged between the open and closed ends. Optionally, the side walls may have a similar length L1 or different lengths. Optionally, the length L1 is in a range of 0.5 mm to 20 mm. The length of the first cavity may typically be in a range from 0.5, 1, 3, 5, 7, 9, 11, 13, 15, 17, or 19 mm up to 1, 3, 5, 7, 9, 11, 13, 15, 17, 19 or 20 mm. Preferably the length L1 is 0.5 to 5.0 mm.

Optionally, the audio head further comprises a second cavity having a length L2, the second cavity is coupled to the first cavity such that the audio unit is arranged between the first and the second cavity. In this regard, the second cavity may be arranged as (namely, serve as) a back cavity (namely, an additional cavity) for the first cavity. Optionally, the length L2 may be same or different from the length L1.

Optionally, the second cavity comprises an attenuator, the attenuator is arranged opposite to the audio unit. In this regard, the attenuator may be arranged in a rear end of the second cavity. Moreover, the rear end is opposite to the closed end and the open end of the first cavity.

Beneficially, the attenuator prevents part of a first audio signal that goes to the second cavity to reflect back to the first cavity and cause an undesired noise. Therefore, said arrangement improves measurement accuracy of the audio head.

The term "audio unit" as used herein refers to an electronic device that generates audio signals in the audio head. Specifically, the audio unit may comprise a combination of a transmitter (such as for generating audio signals) and a receiver (such as for receiving corresponding signals. In this regard, the audio unit is configured to provide, from the closed end where it is placed, a first audio signal will propagate towards the open end of the first cavity, i.e. towards the target, with the first frequency, and receive the second audio signal in response to the first audio signal, i.e. from the target back to the audio head. The terms "first audio signal" and "second audio signal" as used herein refer to representations of sounds using either a changing level of electrical voltage for analog signals, or a series of binary numbers for digital signals. The terms "first frequency" as used herein refer to the number of audio waves of the first audio signal that passes a fixed point in a unit time. In other words, the first frequency may be defined as the number of cycles or vibrations undergone during one unit of time by the first audio signal in a periodic motion. It will be appreciated that, when in use, the open end is placed in contact with a target, such as a skin, when in use. Moreover, the target and the first cavity of the body form a closed space such as a resonator volume. Beneficially, the resonator volume possesses an ability to absorb sound waves, i.e. the first audio signal and the second audio signal, of the resonance frequency and/or vary the resonance frequency. Optionally, the change in the resonance frequency may lead to a change in the phase shift of the first audio signal and the second audio signal. Optionally, said change in the phase shift may be adjusted to achieve an acceptable sound insulation effect at a low-frequency band.

Optionally, the first audio signal may be in a form a standing wave. Herein the standing wave refers to a combination of two audio waves moving in opposite directions, each having the same amplitude and frequency. The said phenomenon is the result of interference; that is, when waves are superimposed, their energies may either be added together or cancelled out. In other words, the standing wave is a wave that oscillates in time but whose peak amplitude profile does not move in space. Moreover, the most common cause of standing waves is the phenomenon of resonance, in which standing waves occur inside the resonator volume due to interference between the audio waves reflected back and forth at the resonator's resonant frequency.

In an example, the standing wave is formed in the first cavity, when the first frequency is selected to be a resonance frequency associated with the first cavity. In an implementation, when measuring the acoustic impedance, the first audio signal may be sent (with a first frequency i.e., a transmitted signal) and the second audio signal is received (received signal i.e., a reflected first signal). The second signal has the same frequency as the first signal i.e., the frequency does not typically change. Additionally, herein the change is a change in phase of the audio frequency and possible amplitude of the second signal in comparison to the first signal.

Optionally, the audio unit comprises an audio source and a microphone configured to provide the first audio signal and receive the second audio signal, respectively. Herein, the audio source and a microphone serve as the transmitter and the receiver of the audio unit. Moreover, the audio source and the microphone are arranged between the first and the second cavity. In an alternative embodiment, the audio source and the microphone may be arranged on the closed end of the first cavity. In an embodiment, the audio source and the microphone may be a same component, i.e. both the audio source and the microphone are implemented in a single audio unit. In another embodiment, the audio source and the microphone may be separate components, i.e. both the audio source and the microphone are implemented as separate components of the audio unit. Beneficially, structure of the audio head enables using the microphone at the same time when the audio head is used with high frequencies to measure the audio impedance (and derive a movement data therefrom) as microphone listens to normal sounds, such as heart sounds.

Optionally, the audio unit is implemented as an audio membrane, optionally a piezo membrane. In this regard, the piezo membrane may be used as a combination of the audio source and the microphone. Beneficially, the piezo membrane provides the first audio signal in a form of a pressure wave towards the target.

Moreover, the audio head comprises a controller. The term "controller" as used herein refers to a software and/or hardware associated with the audio head that is operable to implement specific algorithms therein. Optionally, the controller may employ a processor configured to perform the abovementioned operations. It will be appreciated that optionally the processor includes, but is not limited to, a microprocessor, a microcontroller, a complex instruction set computing (CISC) microprocessor, a reduced instruction set computer (RISC) microprocessor, a very long instruction word (VLIW) microprocessor, or any other type of processing circuit. Furthermore, the term "processor" may refer to one or more individual processors, processing devices and various elements associated with the controller. Additionally, the one or more individual processors, processing devices and elements are arranged in various architectures for responding to and processing the instructions that drive the audio head.

In this regard, the controller is configured to performing operations such as adjusting the first frequency to the resonance frequency value determined by the dimensions of the first cavity. The term "resonance frequency" as used herein refers to the oscillation of the audio signals, such as the first audio signal and the second audio signal, at its natural or unforced resonance.

Optionally, an audio frequency is adjusted (at least partly) based on the length L1. It will be appreciated that the length L1 is inversely proportional to the audio frequency. Moreover, the audio frequency is selected to be to be in resonance with the first cavity. Optionally, the length L1 may be adjusted depending on the used audio frequency. Technical effect of adjusting the audio frequency as function of length L1 is that L1 might have variation depending on the manufacturing tolerances and particularly as the L1 changes depending on the target. If the target (tissue) is soft then it is likely that part of the skin penetrates in the first opening thus shortening the L1. On the other hand if the target (tissue) is harder such as with skinny people then the L1 is longer. In addition pressure applied with the audio unit towards target (by user such as doctor) impacts the length L1. Further, when determining the audio frequency other factors such as material choices of the body and audio unit has an impact on the audio frequency.

Optionally, the audio frequency is in a range of 20 kHz to 100 kHz. In this regard, the audio frequency may typically be in a range of 20, 30, 40, 50, 60, 70, 80, or 90 kHz up to 30, 40, 50, 60, 70, 80, 90, or, 100 kHz. Optionally, the audio frequency may be in a form of a sine wave having frequency range of 20 kHz to 100 kHz.

In an example, the length L1 of the first cavity may be calculated using a formula such as L1=n×D/2. Herein, D is a wavelength of the audio wave and may be calculated using D=v/f, wherein v is speed of sound in air (such as 331 m/sec). Moreover, when the aforementioned values may be applied in the formula then at a frequency of 20 kHz, the length L1 of the first cavity is 0.82 cm (L1=331/20 k/2=0.82 cm) with n=1. In another example, when the frequency is increased to 100 kHz, the length L1 of the first cavity decrease to 0.16 cm (331/100 k/2=0.16 cm) with n=1.

Moreover, the controller is configured to determining acoustic impedance of the target, arranged to be in contact with the open end when in use, using the first audio signal and the second audio signal. Herein, the acoustic impedance refers to a measure of opposition of acoustical flow due to an acoustic pressure. Moreover, the acoustic impedance indicates the amount of sound pressure generated by the vibration of molecules of a particular acoustic medium at a given frequency and could be a characteristic of the medium. In addition, the acoustic impedance is proportional to the length of the cavity, i.e., the local movement of the target, such as the skin, and thus the sounds coming from the subject's body. In general acoustic impedance can be considered as changes in amplitude and phase of the second audio signal. The phase in relation to the first signal in particular. Alternative notation for the acoustic impedance (signal) is usage of A+Bi format where in A is real part and B is imaginary part of the acoustic impedance. In deed using said definition vector length (square root of (A^2+B^2)) can be used to create a first type of indicator value. Phase difference i.e. arctan (B/A) can be used to create a second type of indicator value.

In an example, when the audio head is directed to the ribs, the first indicator value (vector length) related to the acoustic impedance may be used to create an indicator for an observer (such as a doctor) to move the audio head to a different part of the subject's body, i.e. on a different location on the skin over the ribs. Optionally, when no hard obstacle are present close by the ribs (such as when measuring between the ribs towards heart) then the second indicator value of the acoustic impedance observes the movements of very large objects that may be observed as modulation. The said modulation signal (i.e., change in phase) may be used to detect the object and its movements. Optionally, the acoustic impedance may also be a function of possible skin movements of the subject's body.

Optionally, the acoustic impedance is determined based on at least a phase shift between the first audio signal and the second audio signal. Using different notation the phase shift can be considered as an angle of a vector of the acoustic impedance (i.e. arctan(B/A when using notations of the previous chapter). In this regard, the first audio signal is directed towards the target and a part of it may reflect back as the second audio signal. Moreover, the second audio signal has the phase shift dependent on the acoustic impedance of the target, i.e. the object being measured. In an example, a movement of heart may impact the reflected second signal. The said movement may cause a change in the length L1 of the first cavity due to for example a movement of the skin as the heart beats, that changes the length L1 of the first cavity. Said change may cause a change of phase of the second audio signal. It will be appreciated that the magnitude of the acoustic impedance is proportional to the length of the cavity, the "hardness" of the nearby object and movement of distant objects. In an implementation, when measuring the acoustic impedance, the first audio signal a (t) may be sent and the second audio signal b (t) may be received. The amplitude and phase of the signal b (t) with respect to the signal a (t) define the acoustic impedance. Moreover, the acoustic impedance may measure the length of the chamber, i.e. the changes in the distance between the audio head and the skin, the proximal fixed object and the distant moving object.

Mathematically, when in use, a current I=I*sin(wt) may be applied as the first audio signal and a voltage of U=Usin (wt+x) may be received (or measured) as the second audio signal using the microphone, with the phase shift of x=x(t). Herein, the phase shift is an indicator of movement of the target (such as the heart) under the skin as a function of time. Moreover, the phase shift between the first audio signal and the second audio signal is detected. When in use, said measurements may be carried out 10's, 100's or 1000's of times per second. Beneficially, the multiple measurements corresponding to the phase shift may be used to determine a movement of heart in real-time.

In an example, the first audio signal may be provided as a pressure wave towards the target, such as the skin or an organ of interest underneath the skin. Herein the first audio signal is provided as $P_{in}(t)$=P sin(wt), wherein P is power of the audio source (transmitter) of the audio unit. In this regard, when the audio wave collides with the target (such as heart muscle of the subject's body), a part of the audio wave reflects back and comes back to the audio unit (audio source or microphone or a combination thereof) with a delay of dt=2 dx/v, wherein v is speed of sound and dx is distance to the target. Moreover, a reflected pressure wave may be calculated as Pref(t)=aPsin(w(t+dt))=aPsin(wt+2wdx/w), wherein a represents amount of reflection (a<1). Furthermore, the phase difference (dphi) is 2wdx/v, i.e., directly proportional to the distance to the target. Additionally, $P_{ref}$(t)=ap*(sin(wt)*cos(dphi)+cos(wt)*sin(dphi). Moreover, when the target is relatively close then the aforementioned equation may be approximated to cos(dphi)=1 and sin(dphi)=dphi and in general may be written as $P_{ref}$(t)=aP*(sin(wt)+dphi*cos(wt)).

Now, when the impedance is measured using a phase sensitive circuit the measured audio signals may be multiplied with sin(wt) and other hand with cos(wt) signals. Moreover, when the target reflects part of the signal (i.e. the first audio signal) back the phase shift related signal (i.e. the second audio signal) is generated and measured using term <$P_{ref}$(t)*cos(wt)>=dphi*<cos(wt)^2>=½*dphi. Said phase shift related signal is proportional to the distance. Furthermore, when the distance is a multiple of wavelength, the result may be a function of multiple wavelengths. Since distance is known (based on physiology) and using above method formfactor, movement of heart may be reconstructed.

Optionally, the target, arranged to be in contact with the open end when in use, is:

- at a first distance from the open end when in a first state thereof; and
- at a second distance from the open end when in a second state thereof, wherein the first distance is different from the second distance.

In this regard, one or more audio heads may be used for measuring the property of the target. In an example, an approximate distance (such as x1 and x2) of the target (such as heart) from the skin surface is known by physiology. Moreover, the phase difference of the first audio head may be 0 and the phase difference of the second audio head may be 30° initially. Moreover, as the heart starts beating, the phase shift of 10 and 15° may occur, respectively. The said change in the phase differences may be used to calculate a change of the distance of x1 and x2 (i.e., d×1 and d×2), respectively. Furthermore, the aforementioned calculation may provide information on movements of the heart and may be used to derive detailed movement information. Additionally, as mentioned above, when such measurements are carried out 10's, 100's or 1000's of times per second, the movement of the heart may be monitored in real time.

Optionally, the controller may be configured to store information associated with the audio head components. Optionally, the store information includes, for example, values of the first frequency and the resonance frequency, dimensions of the first cavity, acoustic impedance of the target, the first and second distances of the target from the open end when the acoustic head is in use, and so forth. Optionally, the said information may be saved to a software file based on which a potential analysis may be performed. Moreover, the controller may be configured to store the said information in a memory associated therewith. Herein, the term "memory" refers to a device or a system that is used to store information for immediate use in a hardware, software, electronic devices, and the like. Optionally the memory may be an in-built memory of the system (such as read-only memory (ROM), random access memory (RAM), and the like) or a memory on a remote server.

Optionally, the audio head may further comprise a charging portion (for example an electric charging portion). The charging portion may be configured to charge a rechargeable power source (such as a battery) of the audio head. The charging portion may be configured to receive an electric power wirelessly from an external electric power source. In this regard, the charging portion may be or comprises one or more coils or windings. A charging portion configured to receive electric power wirelessly may result in a simpler charging process, for example simply placing the audio head within a pre-determined distance of an external electric power source. Alternatively, the charging portion may be configured to receive an electric power from an external electric power source using a wired charging connector. In this regard, the charging portion may be physically connected to a port, such as by using a pogo pin or a USB charging cable.

The present disclosure also relates to the sensor head as described above. Various embodiments and variants disclosed above apply mutatis mutandis to the sensor head.

The sensor head comprises one or more audio heads. In this regard, the sensor head may employ one or more audio heads (such as 2, 3, 4, 5, 6, 7, 8, 9, 10, 15, 20, 40, and so forth) associated therewith for measuring the property of the target. Optionally, the one or more audio heads are according to the aforementioned audio head, i.e. the one or more audio heads comprising a body having a first cavity; an audio unit; and a controller.

In an exemplary implementation, the sensor head may comprise three audio heads arranged thereon. Optionally, the sensor head may comprise other measurement means such as an electrocardiogram (ECG) contact. Moreover, the sensor head may provide signal to the controller.

Optionally, the sensor head further comprises a flexible ring surrounding an open end of each of the one or more audio heads. In this regard, the flexible ring may provide a closed volume defined by the first cavity of the audio head, the flexible ring and the target (such as the skin of the subject's body), when in use.

Optionally, the sensor head is coupled to a controller configured to determine an acoustic impedance based on the first audio signal and the second audio signal, the controller provides the acoustic impedance to a computing unit via a communication network, wherein the computing unit is configured to employ the acoustic impedance to analyse the property of the target. Herein, the controller may be one or distinct controllers associated with the one or more audio heads. The computing unit may for example be a server or a processor associated with a user device associate with a user of the sensor head. Herein, the computing unit may employ algorithms and artificial intelligence or machine learning tools to analyse provided measurement data (namely acoustic impedance) and use the same to monitor the target in real-time or as a function of time.

Optionally, the user may be a healthcare professional, such as a doctor, a trained technician, and so forth performing measurement using the sensor head. Optionally, the user device may be a computer monitor, a laptop, a mobile phone, and so forth coupled to the sensor head to display results obtained thereby.

Optionally, the communication network may be an individual network, or a collection of individual networks, interconnected with each other and functioning as a single large network. Such individual networks may be wired, wireless, or a combination thereof. Examples of such individual networks include, but are not limited to, Local Area Networks (LANs), Wide Area Networks (WANs), Metropolitan Area Networks (MANs), Wireless LANs (WLANs), Wireless WANS (WWANs), Wireless MANS (WMANs), the Internet, second generation (2G) telecommunication networks, third generation (3G) telecommunication networks, fourth generation (4G) telecommunication networks, and Worldwide Interoperability for Microwave Access (WiMAX) networks. It may be evident that the communication means of the controller may be compatible with a communication means of the computing unit, in order to facilitate communication therebetween.

The present disclosure also relates to the method as described above. Various embodiments and variants disclosed above apply mutatis mutandis to the method.

Optionally, the method comprises providing the acoustic impedance to a computing unit via a communication network, wherein the computing unit is configured to employ the acoustic impedance to analyse the property of the target.

Optionally, the analysis comprises at least one of using a length of a vector of the acoustic impedance as an indication of close by hard objects associated with the target; and/or using an angle of the vector the acoustic impedance as an indication of movements of organ.

In this regard, mathematically the acoustic impedance is calculated using a formula $Z(t)=R(t)+IX(t)$, wherein Z denotes the acoustic impedance, R denotes the acoustic resistance and X denotes the acoustic reactance. Moreover, the acoustic impedance is a complex number having the acoustic resistance R(t) as a real number part and the acoustic reactance X(t) as an imaginary number part thereof. Furthermore, for example, the acoustic reactance is a form of opposition that occurs due to the presence of hard objects associated with the target. Additionally, the acoustic resistance is a form of opposition that occurs due to the movements of organ. The length of the vector can be thus refined as square root of (R(t)^2+X(t)^2) and the angle can be defined as arctan (X(t)/R(t).

The present disclosure also relates to the device as described above. Various embodiments and variants disclosed above apply mutatis mutandis to the device.

The device for measuring a property of a heart, the device comprises the aforementioned audio head. In this regard, the device may be a hand-held non-invasive device that enables effective diagnosis or measurement of various properties of the heart of the human body.

Moreover, the properties of the heart may include the rhythm or the movement of heart such as the rate at which the heart is contracting and expanding, the blood pressure or the flow of blood inside the blood vessels of the heart, and so forth. In an example, the device may record the sound waves (i.e. the first audio signal and the second audio signal) generated by the different sections of the heart and translate the recorded sound waves into corresponding electrical signals for further processing and analysis to provide an effective diagnosis or measurement of the property of the heart.

Optionally, the audio head is used as a stethoscope to listen to heart and as an acoustic impedance measurement audio head to detect movements of the heart. In this regard, the stethoscope is employed for listening to internal sounds of the heart. Typically, the stethoscope may have a small disc-shaped resonator that is placed against the skin, and one or two tubes connected to two earpieces/audio heads. Additionally, the stethoscope works on the principle of reflection of sound, the vibration causes a diaphragm to vibrate. Notably, the diaphragm vibrates when sound occurs and the high-frequency sounds travel up the hollow plastic tubing into hollow metal earpieces associated therewith. Beneficially, the audio head may be used as stethoscope as well as the microphone at the same time when the stethoscope is measuring and the microphone is sending ultrasound normal sounds from 10 Hz to 5 khz. Advantageously, said arrangement may enable the same audio head to be used for two purposes at the same time. For example, a doctor may listen to exactly same place when the ultra-measurement is done using the said microphone.

Moreover, when used as the acoustic impedance measurement audio head, the audio head may detect movements of the heart. As mentioned above, when such measurements are carried out 10's, 100's or 1000's of times per second, the movement of the heart may be monitored in real time, and a simulation model of the heart may be generated for experimentation, research and diagnoses purposes.

Overall the provided audio head can be used as a component for a sensor head. The sensor head can be used as module of a device. The device can be used for example to measure a property of a heart. An example property is using the device to form three dimensional image of heart or for example measuring at heart movements. Technically the audio head provides audio signal to target (person) and acoustic impedance is measured. The acoustic impedance can be used as data for measuring (or determining) properties. Further changes on acoustic impedance as function time can provide temporal information of the properties of heart (or other organ).

DETAILED DESCRIPTION OF THE DRAWINGS

Referring to FIG. 1, illustrated is a schematic illustration of an audio head 100, in accordance with an embodiment of the present disclosure. The audio head 100 comprises a body 102 having a first cavity 104, the first cavity 104 having an open end 106 and a closed end 108 opposite to the open end 106 separated by a length L1. Moreover, the audio head 100 comprises an audio unit 110 arranged on the closed end 108, wherein the audio unit 110 is configured to provide a first audio signal (not shown), the first audio signal directed towards the open end 106 with a first frequency, and receive a second audio signal. In practice the first audio signal propagates to all direction but preferably the audio unit and the body of the audio head is arranged in a way that "main" direction of the first audio signal is towards the open end. Furthermore, the audio head 100 comprises a controller (not shown) configured to adjust the first frequency to a resonance frequency value determined by the dimensions of the first cavity 104 and determine acoustic impedance of a target 112, arranged to be in contact with the open end 106 when in use, using the first audio signal and the second audio signal, wherein the second audio signal comprises at least a part of the first audio signal that is reflected back from the target 112.

Additionally, the audio head 100 further comprises a second cavity 114 having a length L2, the second cavity 114 is coupled to the first cavity 104 such that the audio unit 110 is arranged between the first 104 and the second cavity 114. Moreover, the second cavity 114 comprises an attenuator 116, the attenuator 116 is arranged opposite to the audio unit 110.

Figure 2:
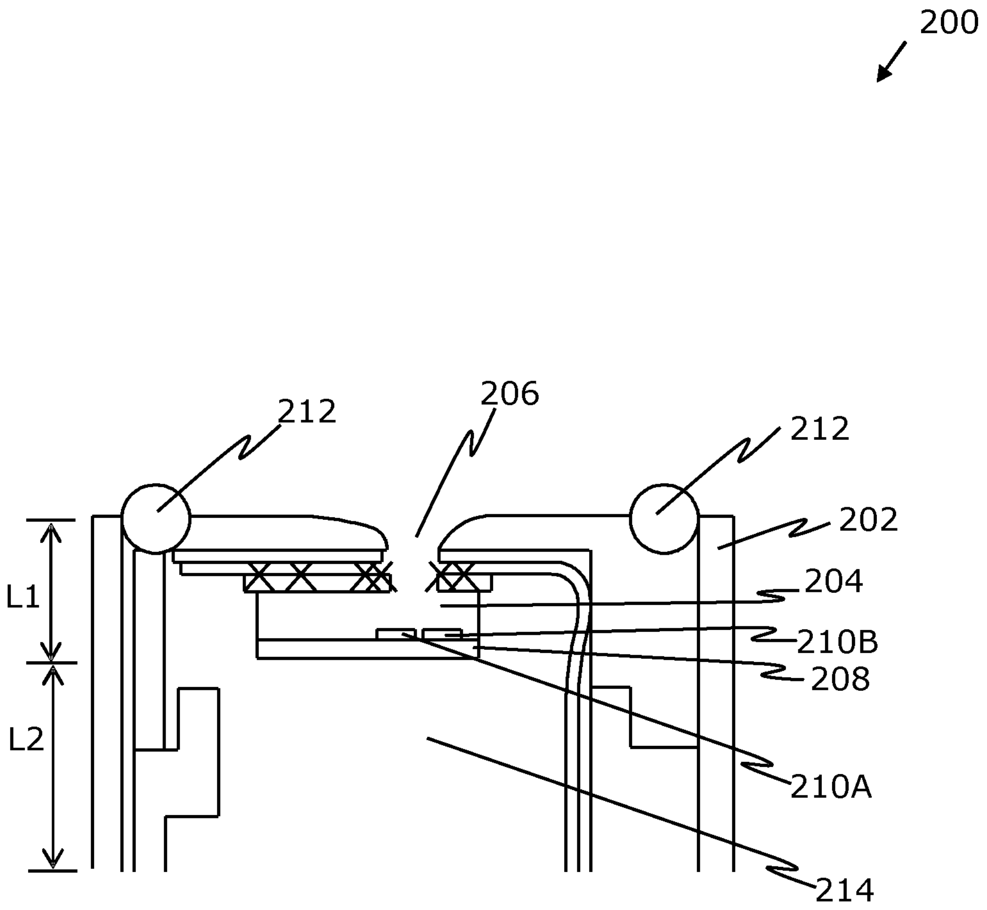
FIG. 2 is a schematic illustration of an audio head, in accordance with another embodiment of the present disclosure.

Referring to FIG. 2, illustrated is a schematic illustration of an audio head 200, in accordance with another embodiment of the present disclosure. The audio head 200 comprises a body 202 having a first cavity 204, the first cavity 204 having an open end 206 and a closed end 208 opposite to the open end 206 separated by a length L1. Moreover, the audio head 200 comprises an audio unit 210A and 210B arranged on the closed end 208, wherein the audio unit 210A and 210B are configured to provide a first audio signal (not shown directed towards the open end 206 with a first frequency, and receive a second audio signal, respectively. Additionally, the audio head 200 further comprises a second cavity 214 having a length L2, the second cavity 214 is coupled to the first cavity 204 such that the audio unit 210A and 210B is arranged between the first 204 and the second cavity 214.

Figure 3:
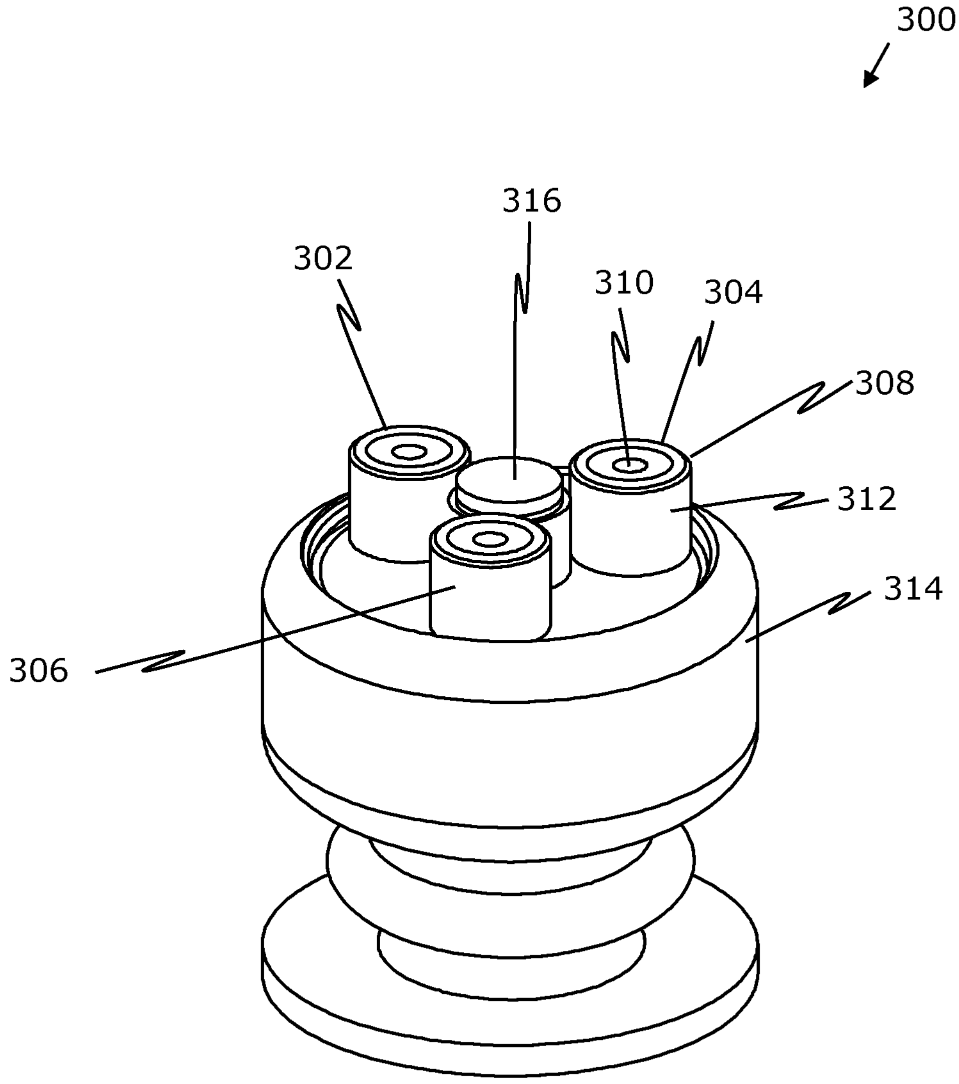
FIG. 3 is a schematic illustration of a sensor head, in accordance with an embodiment of the present disclosure.

Referring to FIG. 3, illustrated is a schematic illustration of a sensor head 300, in accordance with an embodiment of the present disclosure. As shown, the sensor head 300 comprises one or more audio heads, such as the audio heads 302, 304, and 306. Moreover, the sensor head 300 further comprises a flexible ring 308 surrounding an open end 310 of each of the audio heads 302, 304, and 306. Furthermore, each of the audio heads 302, 304, and 306 have a body 312. Furthermore, the sensor head 300 comprises a body 314. As shown, the sensor head 300 further comprises an electrocardiogram (ECG) contact 316.

Figure 4A:
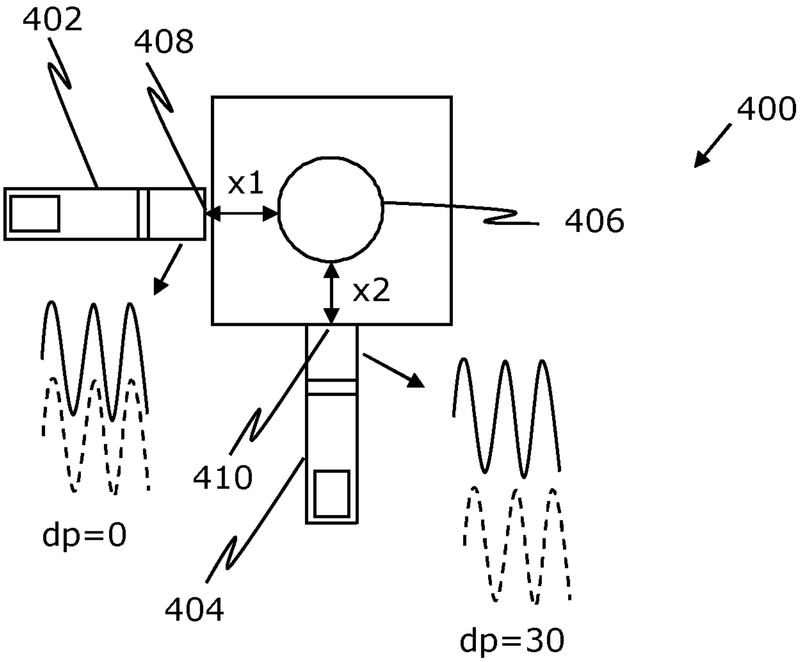
FIGS. 4A and 4B are exemplary implementation of an audio head for analysing a property of a target, in accordance with an embodiment of the present disclosure.
Figure 4B:
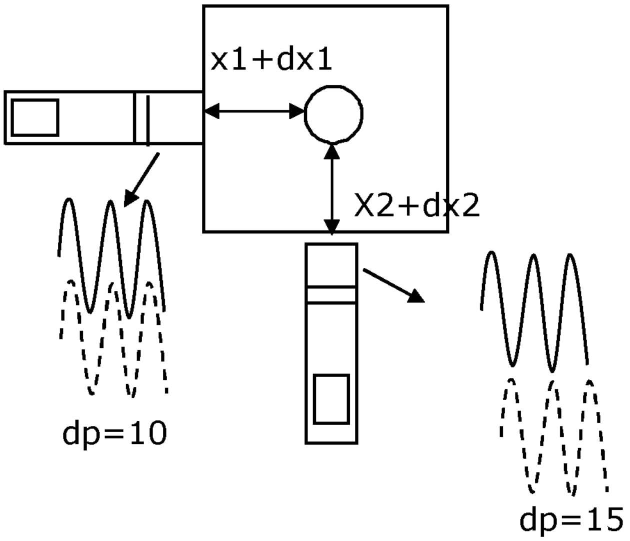

Referring to FIGS. 4A and 4B, illustrated is an exemplary implementation 400 of audio heads 402, 404 for analysing a property of a target 406, in accordance with an embodiment of the present disclosure. As shown, the audio heads 402, 404 are arranged to be in contact, with open ends 408 and 410 thereof, respectively when in use, with the target 406. As shown in FIG. 4A, the open ends 408, 410 of the corresponding audio heads 402, 404 are arranged at a first distance, x1 and x2, respectively, from the target 406 when in a first state, i.e. when for example the target is in a relaxed (or expanded) state thereof. As shown in FIG. 4B, the open ends 408, 410 of the corresponding audio heads 402, 404 are arranged at a second distance, x1+d×1 and x2+d×2, respectively, from the target 406 when in a second state, i.e. when for example the target is in a contracted state thereof, wherein the first distance is different from the second distance.

Figure 5:
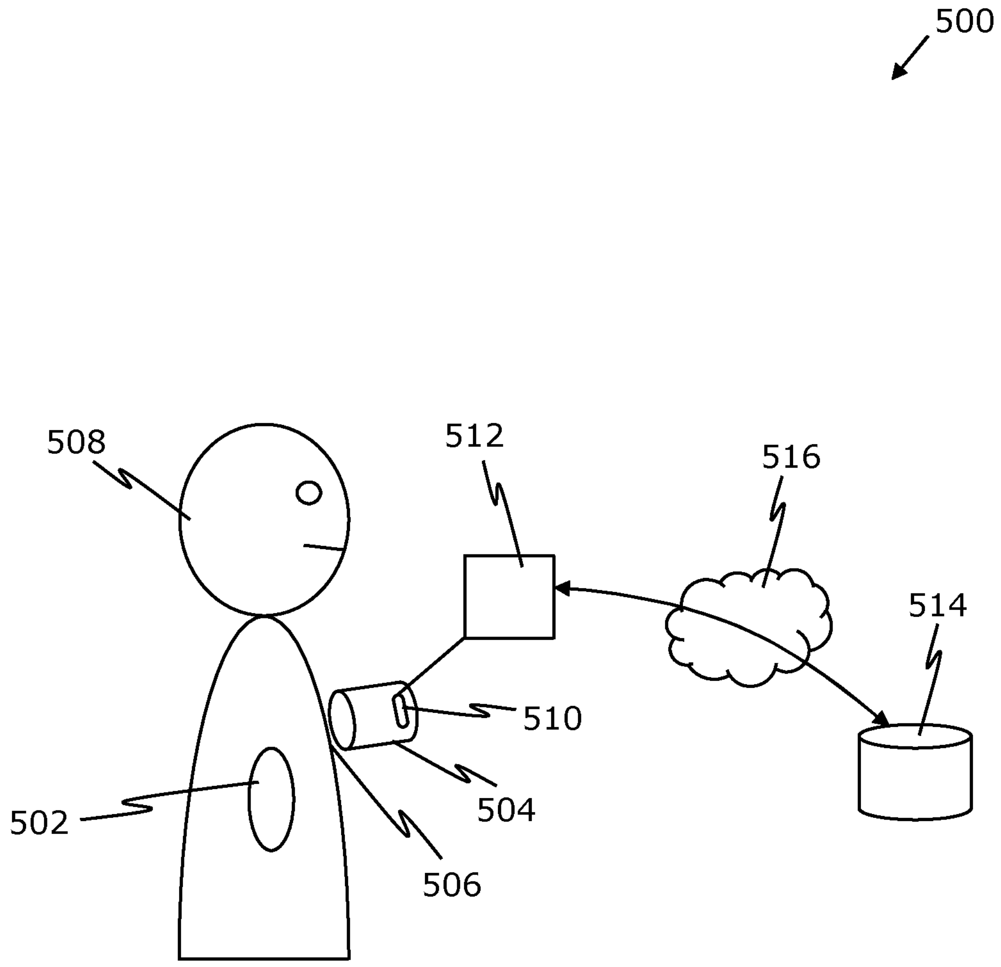
FIG. 5 is a schematic illustration of an audio head analysing a property of a target, in accordance with another embodiment of the present disclosure.

Referring to FIG. 5, illustrated is a schematic illustration of an environment 500 showing a device for measuring a property of a heart 502 comprising an audio head 504, in accordance with another embodiment of the present disclosure. As shown, the audio head 504 is arranged in contact with a skin 506 of a subject 508 to measure the properties of the heart 502 underneath the skin 506. The audio head 504 comprises an audio unit 510 arranged on a closed end of a first cavity of the audio head 504. Moreover, an open end of the audio head 504 is in contact with the skin 506 of the subject 508, when in use.

Furthermore, the audio unit 510 is coupled to a controller 512 that provides the acoustic impedance to a computing unit 514 via a communication network 516, wherein the computing unit 514 is configured to employ the acoustic impedance to analyse the property of the heart 502.

Figure 6:
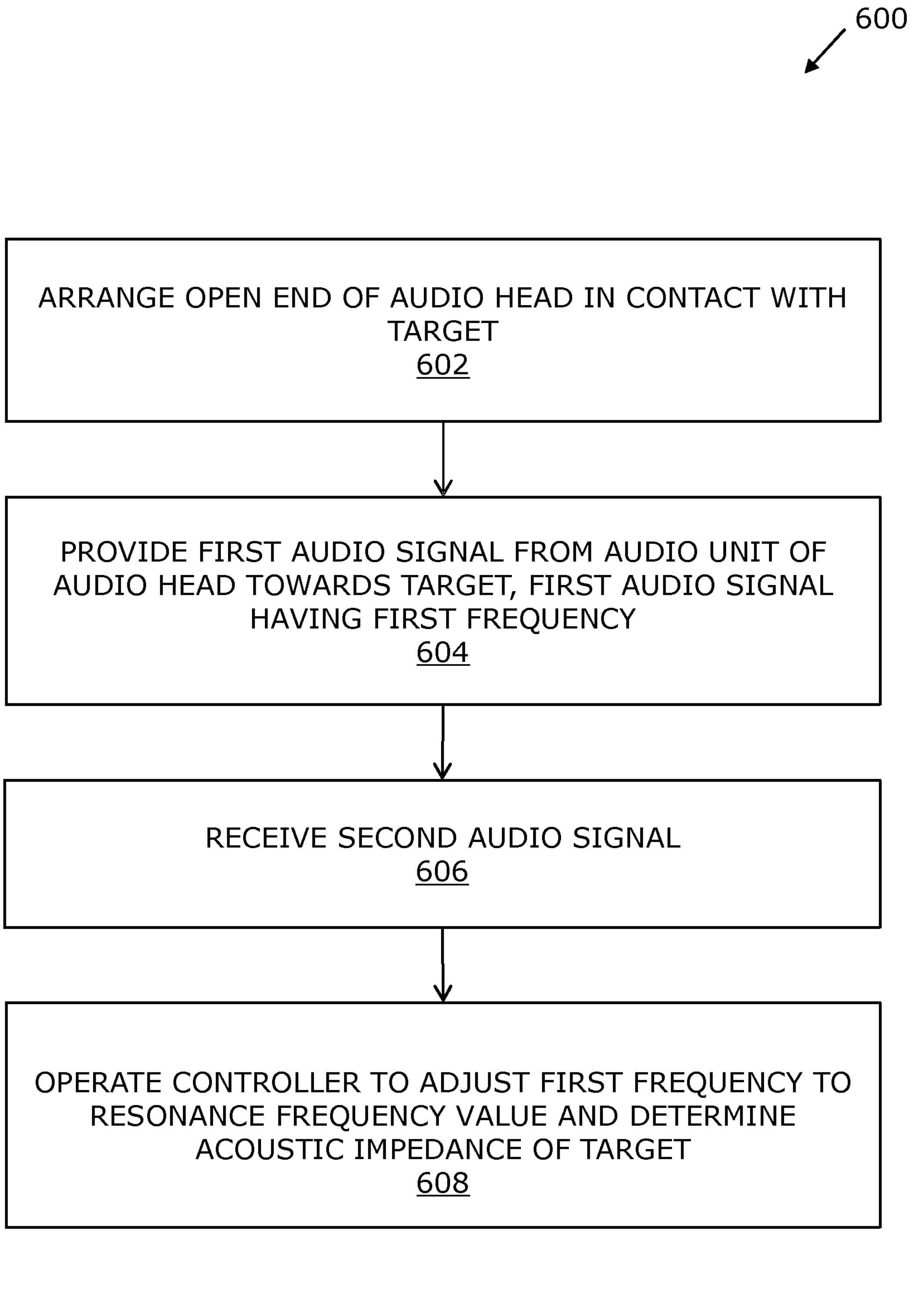
FIG. 6 is a flowchart depicting steps of a method of analysing a property of a target, in accordance with an embodiment of the present disclosure.

Referring to FIG. 6, illustrated is a flowchart 600 depicting steps of a method of analysing a property of a target, in accordance with an embodiment of the present disclosure. At step 602, an open end of an audio head is arranged in contact with the target. At step 604, a first audio signal from an audio unit of the audio head is provided towards the target, the first audio signal having a first frequency. At step 606, a second audio signal from the target is received towards the audio unit. At step 608, a controller is operated to adjust the first frequency to a resonance frequency value determined by the dimensions of a first cavity of the audio head, and determine acoustic impedance of the target arranged to be in contact with the open end when in use using the first audio signal and the second audio signal, wherein the second audio signal is a part of the first audio signal that is reflected back from the target in real time.

The steps 602, 604, 606 and 608 are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. An audio head comprising
- a body having a first cavity, the first cavity having an open end and a closed end opposite to the open end separated by a length L1;
- an audio unit arranged on the closed end, wherein the audio unit is configured to
- provide a first audio signal, the first audio signal having a first frequency, and
- receive a second audio signal; and
- a controller configured to
- adjust the first frequency to a resonance frequency value determined by the dimensions of the first cavity; and
- determine acoustic impedance of a target, arranged to be in contact with the open end when in use, using the first audio signal and the second audio signal,
- wherein the second audio signal comprises at least a part of the first audio signal that is reflected back from the target;
- the audio head further comprising a second cavity having a length L2, the second cavity coupled to the first cavity such that the audio unit is arranged between the first and the second cavity,
- wherein the second cavity comprises an attenuator, the attenuator is arranged opposite to the audio unit.

2. The audio head according to claim 1, wherein the acoustic impedance is determined based on at least a phase shift between the first audio signal and the second audio signal.

3. The audio head according to claim 1, wherein the audio unit comprises an audio source and a microphone configured to provide the first audio signal and receive the second audio signal, respectively.

4. The audio head according to claim 1, wherein the audio unit is implemented as an audio membrane, optionally a piezo membrane.

5. The audio head according to claim 1, wherein the length L1 is in a range of 1 mm to 20 mm.

6. The audio head according to claim 1, wherein an audio frequency is adjusted based on the length L1.

7. The audio head according to claim 6, wherein the audio frequency is in a range of 20 kHz to 100 kHz.

8. The audio head according to claim 1, wherein the target, arranged to be in contact with the open end when in use, is:
- at a first distance from the open end when in a first state thereof; and
- at a second distance from the open end when in a second state thereof, wherein the first distance is different from the second distance.

9. A sensor head comprising one or more audio heads, wherein the one or more audio heads are according to claim 1.

10. The sensor head according to claim 9, further comprising a flexible ring surrounding an open end of each of the one or more audio heads.

11. The sensor head according to claim 9, wherein the sensor head is coupled to a controller configured to determine an acoustic impedance based on the first audio signal and the second audio signal, the controller unit provides the acoustic impedance to a computing unit via a communication network, wherein the computing unit is configured to employ the acoustic impedance to analyse a property of a target.

12. A device for measuring a property of a heart, the device comprising an audio head of claim 1.

13. The device according to claim 12, wherein the audio head is used as stethoscope to listen to heart and as an acoustic impedance measurement audio head to detect movements of the heart.

14. A method of analysing a property of a target, the method comprises arranging an open end of an audio head in contact with the target;

providing a first audio signal from an audio unit of the audio head towards the target, the first audio signal having a first frequency;

receiving a second audio signal from the target towards the audio unit; and operating a controller configured to adjust the first frequency to a resonance frequency value determined by the dimensions of a first cavity of the audio head, and determine acoustic impedance of the target, arranged to be in contact with the open end when in use, using the first audio signal and the second audio signal, wherein the second audio signal comprises at least a part of the first audio signal that is reflected back from the target, wherein the method comprises providing the acoustic impedance to a computing unit via a communication network, wherein the computing unit is configured to employ the acoustic impedance to analyse the property of the target, wherein the analysis comprises at least one of using a length of a vector of the acoustic impedance as an indication of close by hard objects associated with the target; and/or using an angle of the vector of the acoustic impedance as an indication of movements of the target/organ.

* * * * *